(12) United States Patent
Yang et al.

(10) Patent No.: US 8,146,189 B2
(45) Date of Patent: Apr. 3, 2012

(54) PATIENT ALIGNMENT DEVICE (75) Inventors: Jun Yang, Drexel Hill, PA (US); Jing Feng, Drexel Hill, PA (US)

(73) Assignee: Jun Yang, Garnet Valley, PA (US), part interest ( * ) Notice: Subject to any disclaimer, the term of this patent is extended or adjusted under 35 U.S.C. 154(b) by 703 days.

(21) Appl. No.: 12/276,895

(22) Filed: Nov. 24, 2008

(65) Prior Publication Data

US 2009/0139030 A1 Jun. 4, 2009

Related U.S. Application Data (60) Provisional application No. 61/004,730, filed on Nov. 30, 2007.

(51) Int. Cl.
*A47B 7/02* (2006.01)
(52) U.S. Cl. ............. 5/618; 5/616; 600/415; 606/245
(58) Field of Classification Search ............. 5/601, 613, 5/616, 617, 618, 81.1 RP, 943; 600/415; 606/245
See application file for complete search history.

(56) References Cited

U.S. PATENT DOCUMENTS

| 1,011,038 A | * | 12/1911 | Davenport | 606/245 |
| 3,620,210 A | * | 11/1971 | Annas et al. | 606/245 |
| 7,189,214 B1 | * | 3/2007 | Saunders | 602/32 |

* cited by examiner

*Primary Examiner* — Robert G Santos
*Assistant Examiner* — Nicholas Polito
(74) *Attorney, Agent, or Firm* — William H. Eilberg (57) ABSTRACT

A patient alignment device includes a table and a rotatable member positioned to rotate relative to the table. The rotatable member may be a head-support plate or a board which supports substantially all of a patient's body. A motor moves the board or plate so as to align the patient's body, or a part of the body, in a desired direction. The board may be formed in two segments, the segments being selectively connectable to each other, the segments also being selectively connectable to the table by pins, at various possible pivot points. Positioning of the pins determines the mode of rotation of the board. The invention allows an operator to align the patient's body with precision, by remote control, and without interrupting the medical procedure.

3 Claims, 6 Drawing Sheets

PATIENT ALIGNMENT DEVICE

CROSS-REFERENCE TO PRIOR APPLICATION

Priority is claimed from U.S. Provisional Patent Application Ser. No. 61/004,730, filed Nov. 30, 2007, the disclosure of which is incorporated by reference herein.

BACKGROUND OF THE INVENTION

The present invention relates to the field of medical procedures, including surgery or other therapy, and diagnostic procedures, and provides a method and apparatus for positioning a patient in a desired orientation.

Radiation therapy, diagnostic imaging, surgery, and other medical procedures often require that a patient's head or body be aligned parallel to the center axis of a table, or other support, or to some other preferred orientation. It may be necessary to align the patient's head or body immediately before, or during, the medical procedure.

It is difficult for the patient to know his own orientation, and the patient may change his or her orientation during the procedure. Therefore, the personnel conducting the procedure need to adjust the patient's orientation manually before the procedure, or to pause the procedure to re-adjust the patient's orientation after the procedure has begun.

The present invention provides a method and device for automatically and precisely adjusting all or a portion of a patient's body, during a medical procedure.

SUMMARY OF THE INVENTION

In one embodiment, the patient alignment device of the present invention comprises a table for supporting a patient, a generally flat rotatable member disposed on the table, and means for rotating the rotatable member in a controlled manner. The rotatable member can be a head-support plate, sized and positioned to support the head of a patient, or it can be a board which supports substantially all of the patient's body.

In one preferred embodiment, the rotating means comprises a step motor, connected to rotate the board or plate by driving a threaded shaft. A connecting member engages the threaded shaft, such that when the shaft rotates, the connecting member moves along the length of the shaft. This translational motion of the connecting member is transmitted to the board or plate, causing the desired rotation.

The board may be formed of a single piece, or it may be formed in two segments. In the embodiment having two segments, the segments may be connected by removable straps or connectors. The board segments are affixed to the table by a plurality of removable pins. Engagement or disengagement of selected pins, and engagement or disengagement of the straps or connectors, determines the mode of rotation of a board segment. In all cases, the board segment is made to rotate about a pin, but the identity of the pin about which the board segment rotates can be changed.

In general, engagement of a pin having a smaller distance from the motor causes a larger angle of rotation, and is useful for patients who are relatively light. Conversely, engagement of a pin having a larger distance from the motor induces a smaller angle of rotation of the board, and is useful when the patient is relatively heavy.

The invention also includes the method of performing a medical procedure, such as surgery or a diagnostic procedure, on a patient who lies on a table. The rotatable member, whether it be a head-support plate or a board which supports the patient's entire body, is moved so as to align the body, or a portion thereof, in the desired direction. The movement of the rotatable member can be accomplished by remote control, and without interrupting the medical procedure. The movement is preferably performed with a step motor, or other motor, capable of precise movements, so as to position the patient accurately.

The present invention therefore has the primary object of providing a patient alignment device.

The invention has the further object of providing an automated method for positioning a patient's body, or a portion thereof, in a desired direction, before and/or during a medical procedure.

The invention has the further object of facilitating medical procedures by eliminating the need for personnel to make manual adjustments of the position of a patient's body.

The invention has the further object of reducing the physical demands imposed on an operator of a medical procedure when it is necessary to adjust the position of the patient's body.

The invention has the further object of providing a method and apparatus which improves the precision and repeatability of a medical procedure.

The invention has the further object of facilitating adjustment of a patient's body during a medical procedure, without interrupting the procedure.

The invention has the further object of providing a method and apparatus for adjustment of portions of a patient's body, wherein the invention can be used with conventional treatment tables.

The reader skilled in the art will recognize other objects and advantages of the present invention, from a reading of the following brief description of the drawings, the detailed description of the invention, and the appended claims.

DETAILED DESCRIPTION OF THE INVENTION

Figure 1:
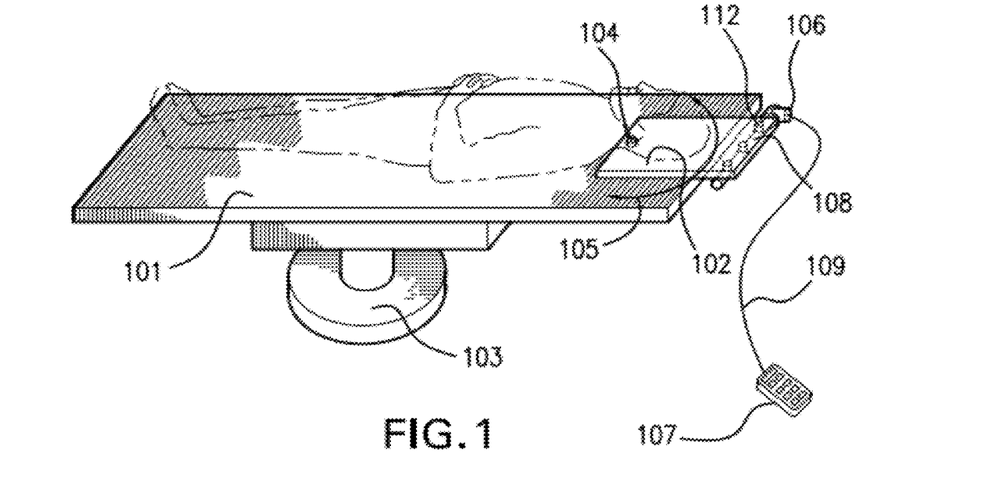
FIG. 1 provides a perspective view showing a patient alignment device, for use in aligning the head of the patient, the drawing showing the patient in phantom, lying on a table which is specially designed according to the present invention.

FIG. 1 provides a perspective view, showing a first embodiment of the patient alignment device of the present invention. The device includes table 101 which is supported by stand 103. A head-support plate 102 is connected to the table by pin 104. The plate 102 can pivot or rotate about the pin.

A motor 106 drives a rotatable threaded shaft 108. Connecting members 112 threadedly engage the threaded shaft, and convert the axial motion of the threaded shaft into translational motion of the connecting members, which in turn move the plate 102. That is, rotation of the threaded shaft causes the plate to pivot in either direction indicated by arrow 105. More details of the structure of the motor, the threaded shaft, and the connecting members are given later, in the discussion of a further embodiment.

The motor is chosen to be capable of bidirectional motion, so that it can rotate the shaft in either direction. In one preferred embodiment, the motor is a step motor.

Remote control device 107 is connected by cable 109 to the motor. The remote control device enables an operator to adjust the position of plate 102 from a distance. The cable 109 can be made longer than what is shown in the drawing. Also, the method of remote control can be wireless, and a wireless remote control system should be deemed the equivalent of what is shown.

A more detailed explanation of the embodiment of FIG. 1 is as follows. The patient lays his or her head on the head-support plate 102. The pin 104, which engages a hole formed near one end of the plate, serves as an axis of rotation. The other end of the plate 102 is connected to the rotatable threaded shaft 108 by connecting members 112. The motor 106 drives the rotatable threaded shaft and thereby pushes or pulls the movable end of the plate 102 so as to cause the plate to pivot about pin 104. The orientation of the patient's head is therefore adjusted by rotation of the plate.

In general, the flexible cervical spine allows a person's head to be rotated by more than ten degrees. In the preferred embodiment of the present invention, the length of the rotatable threaded shaft is chosen to allow rotation by only a few degrees, and fewer than ten degrees, in either direction. The latter limit is established for purposes of safety of the patient. To this end, the plate 102 is equipped with a stopper (described later) to prevent movement of the plate beyond a predetermined angular limit. The rotatable threaded shaft could be a gear wheel, or a pulley (formed either by a belt or a chain), or any other equipment that can transmit the power of the motor to the plate.

All of the parts used to make the device of the present invention must be made from material which does not affect the medical procedure. For example, if the procedure is radiation therapy or medical imaging, at least some of the parts should not be made of metal. The head-support plate 102 must be sufficiently strong to support the patient's head. The plate must be sufficiently glossy to avoid excessive friction. The movement of the motor 106 must be sufficiently precise to produce a precisely controlled movement of the plate, to meet the requirement of alignment of the patient's head. The power output of the motor must be sufficient to fulfill the objective of moving the plate while the patient's head rests thereon. But the voltage used to drive the motor must nevertheless be in a safe range.

For the reasons given above, the plate 102 and the pin are preferably made of plastic. But these components could be made of any other sufficiently rigid material, such as wood. Also, to the extent that doing so would not interfere with the contemplated medical procedure, such components could be made of metal.

Figure 2:
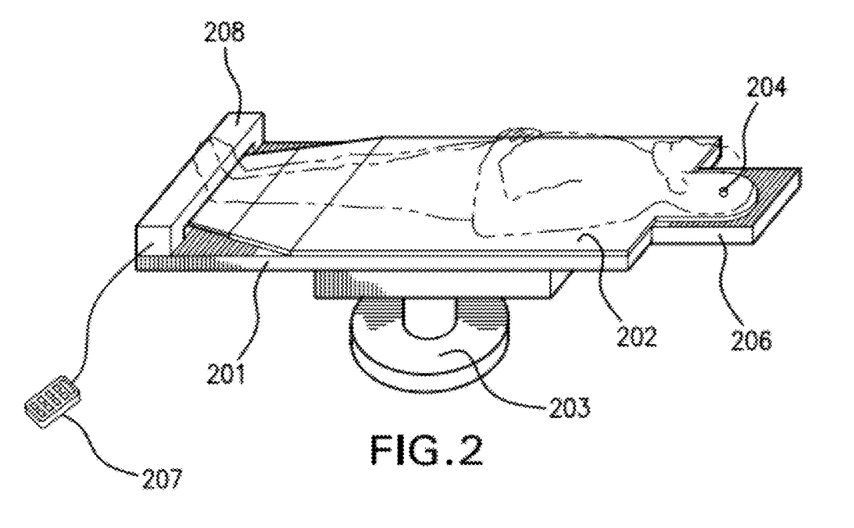
FIG. 2 provides a perspective view showing a patient alignment device of the present invention, for use in aligning the body of the patient, the drawing also showing a patient in phantom.

FIG. 2 shows another embodiment of the present invention, wherein the device moves substantially the entire body of the patient. The device includes table 201 which is supported by stand 203. Board 202 is supported by the table. The table includes plate 206, which supports the head of the patient as shown. Pin 204 provides a pivot point for the board.

The board 202 is moved in the same manner as described with respect to FIG. 1. It is preferred that the motor, and the rotatable threaded shaft, and their associated components, be covered by an appropriate housing, for reasons of both esthetics and safety. Such a housing is not shown in FIG. 1, for purposes of illustration, but housing 208 is shown in FIG. 2. The movement of the board in FIG. 2 is achieved in the same manner as the movement of plate 102 of FIG. 1. Remote control device 207 controls the operation of the motor disposed within the housing.

A more detailed description of the operation of the embodiment of FIG. 2 is as follows. The patient lies on board 202. The pin 204, which is engaged with a hole at one end of the board 202, serves as a pivot point, or axis of rotation, for the board. The plate 206 reinforces the pin 204 if necessary. The other end of the board is connected to the rotatable threaded shaft (not visible in FIG. 2). The motor contained within housing 208 drives the threaded shaft, and thereby pushes or pulls the movable end of the board 202, causing the board to rotate about pin 204. Thus, rotation of the board causes alignment of the patient's body.

The length of the threaded shaft is chosen so as to allow rotation of the patient's body by only a few degrees in either direction, for reasons of safety. A rotation stopper (not shown) prevents movement beyond a predetermined angular limit. As in the embodiment of FIG. 1, the threaded shaft could be a gear wheel or pulley, or any equipment that can transmit power from the motor to the board.

As in the embodiment of FIG. 1, all parts must be made from material which does not affect the medical procedure. If the procedure includes radiation therapy or medical imaging, it may be necessary to form some parts of non-metallic materials. The board 202 must be sufficiently strong to support the patient's body. The board must be sufficiently glossy to avoid excessive friction. The motor must be capable of sufficiently precise movements to allow an operator to align the patient's body with precision. The motor must have sufficient power output to support the payload, i.e. to move the entire board, with the patient's body. But the voltage used should nevertheless be in a safe range.

As in the embodiment of FIG. 1, the board 202, the pin 204, and the plate 206 are preferably made of plastic, but they could instead be made from any sufficiently rigid material such as wood. If doing so would not interfere with the contemplated medical procedure, the components could also be made of metal.

Figure 3:
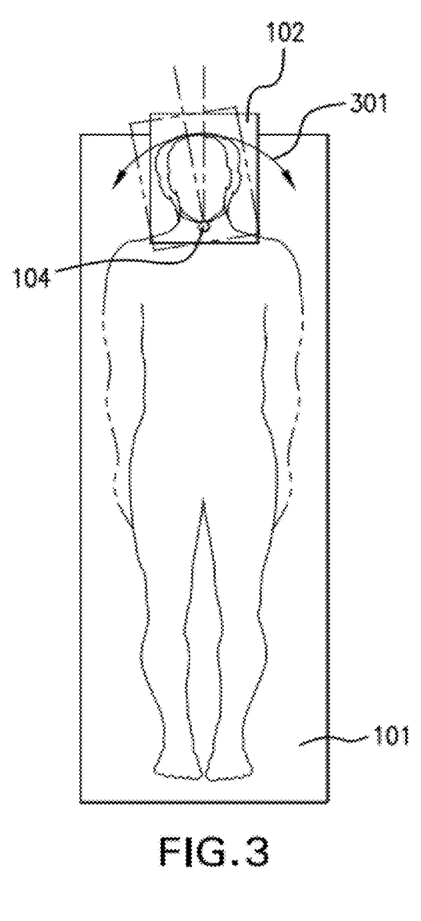
FIG. 3 provides a simplified plan view of the head alignment device of FIG. 1, illustrating the adjustment of the position of the patient's head.

The simplified plan view of FIG. 3 shows the adjustment of the position of the patient's head, using the embodiment of FIG. 1. FIG. 3 shows how head-support plate 102 rotates about pin 104, in either direction, as illustrated by arrow 301. The amount of rotation may be exaggerated in the figures, for purposes of illustration.

Figure 4:
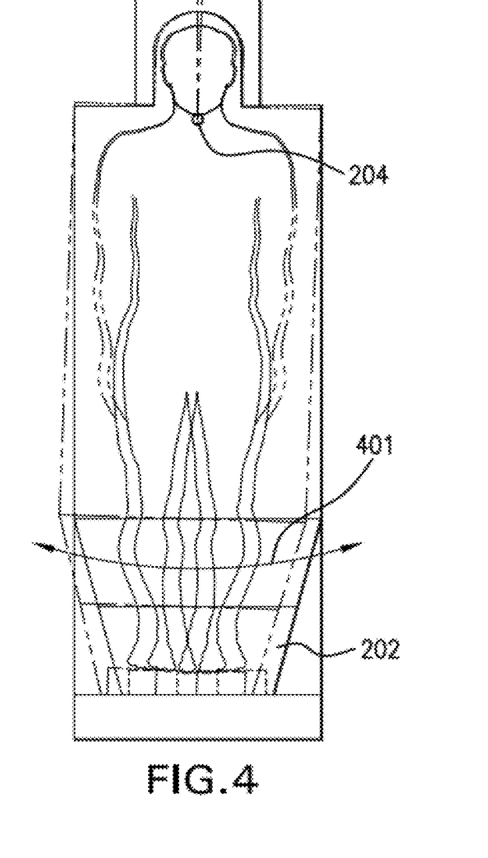
FIG. 4 provides a simplified plan view of the body alignment device of FIG. 2, illustrating the adjustment of the position of the patient's body.

Similarly, the simplified plan view of FIG. 4 shows the adjustment of the position of the patient's body, using the embodiment of FIG. 2. FIG. 4 shows how the entirety of board 202 rotates about pin 204, in either direction, as illustrated by arrow 401. The amount of rotation may be exaggerated for purposes of illustration.

Both of the embodiments of FIGS. 1 and 2 therefore include a rotatable member. In FIG. 1, the rotatable member is head-support plate 102. In FIG. 2, the rotatable member is board 202, which extends along the majority of the length of the table. In both cases, the rotatable member has a generally flat surface which is substantially parallel to the surface of the table.

In each of the embodiments of both FIGS. 1 and 2, there is only one mode of rotation. In the embodiment of FIG. 1, the head-support plate is the only component, in contact with the patient, which can rotate. In the embodiment of FIG. 2, the board 202 rotates only about pin 204, thus causing rotation of the entire body of the patient.

Figure 5:
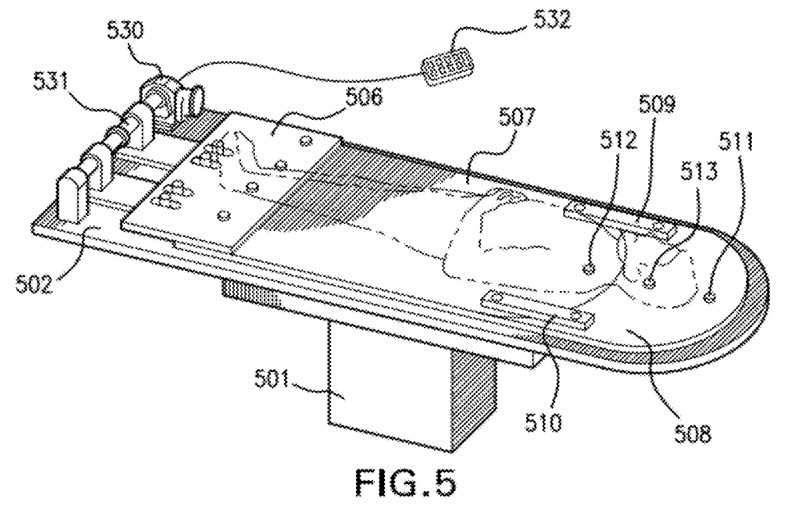
FIG. 5 provides a perspective view of another embodiment of the present invention, wherein the table includes two distinct segments.
Figure 6:
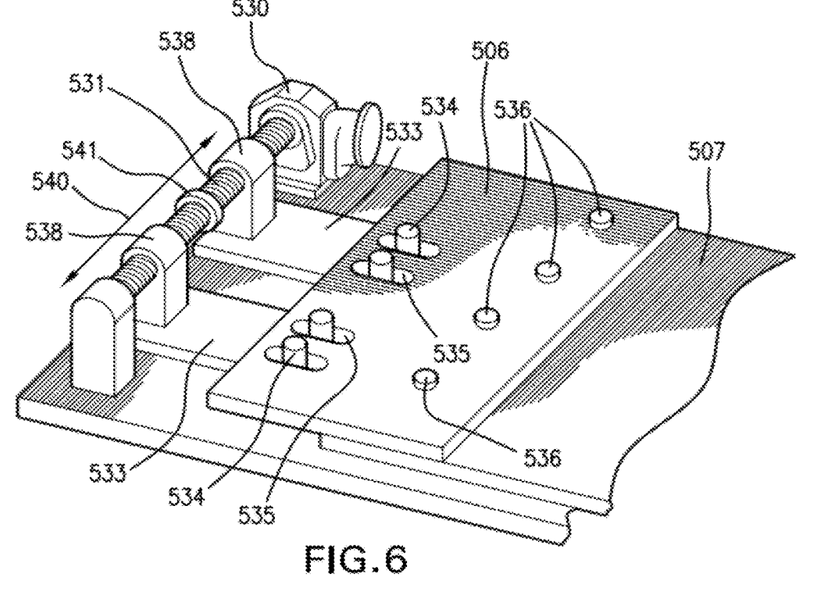
FIG. 6 provides a fragmentary perspective view of the motor and threaded rotatable shaft which provide the adjustments used in the present invention.

FIGS. 5 and 6 illustrate another embodiment of the present invention, wherein the board is constructed of two pieces or segments. Table 502 is supported by stand 501. The board holding the patient includes first board segment 507 and second board segment 508. Board segment 506 is rigidly attached to first board segment 507, and serves as a means for engagement with the motor, as will be described later.

As shown in FIG. 5, the first and second board segments include mating curved edges, such that one segment may rotate while the other is fixed, when the segments are not joined together. For example, when second board segment 508 is fixed, first board segment 507 can rotate while its curved edge remains in abutment with the mating curved edge of segment 508.

The first and second board segments may be held together by straps or connectors 509 and 510. The device also includes pins 511, 512, and 513, the functions of which will be described below. The motor 530, which drives rotatable threaded shaft 531, can be controlled by remote control device 532. The remote control device is shown as a wired connection, but a wireless connection may be substituted.

FIG. 6 shows details of the motor, the threaded shaft, and related components. Connecting members 538 engage threaded shaft 531. Rotation of the shaft, by motor 530, causes these connecting members to move along the length of the shaft, due to the threaded engagement of the connecting members with the shaft. The connecting members are rigidly attached to bases 533, which are connected to pins 534. The pins 534 engage holes 535 formed in board 506. Board 506 is rigidly connected to first board segment 507 through pins 536.

When the motor turns the threaded shaft 531, the connecting members 538 move in either direction along the length of the shaft, depending on the direction of rotation of the shaft, due to their threaded engagement with the shaft. The axial motion of the connecting members is indicated by arrow 540. Stopper 541 prevents the connecting members from moving beyond a predetermined distance, and therefore limits the angle through which the board or board segment can be rotated.

Although the details of the motor and threaded shaft, and connecting members and stopper are shown with respect to the embodiment of FIG. 5, it should be understood that the same arrangement can be used in the embodiments of FIGS. 1 and 2. That is, the motor, threaded shaft, connecting members, and stopper, can all be substantially the same in all of these embodiments. Stated in other words, the components to the left of board 506, in FIG. 6, can be deemed to apply to all embodiments.

As in the embodiments of FIGS. 1 and 2, the motor and threaded shaft are preferably encased within a housing. These components are shown without a housing, in FIGS. 5 and 6, for purposes of illustration.

The embodiment of FIG. 5 can operate in two primary modes, discussed below. Each mode of operation is determined by the configuration of connectors and pins.

The first mode of operation, of the embodiment of FIG. 5, is the rotation of the entire body of the patient. In this mode, connectors 509 and 510 are affixed, so that first board segment 507 and second board segment 508 are joined. Thus, the two segments effectively merge into one large board. The motor rotates this large board around either pin 511, pin 512, or pin 513. Only one pin, among pins 511, 512, and 513, is locked at any given time, the other two pins being removed.

Figures 7, 8:
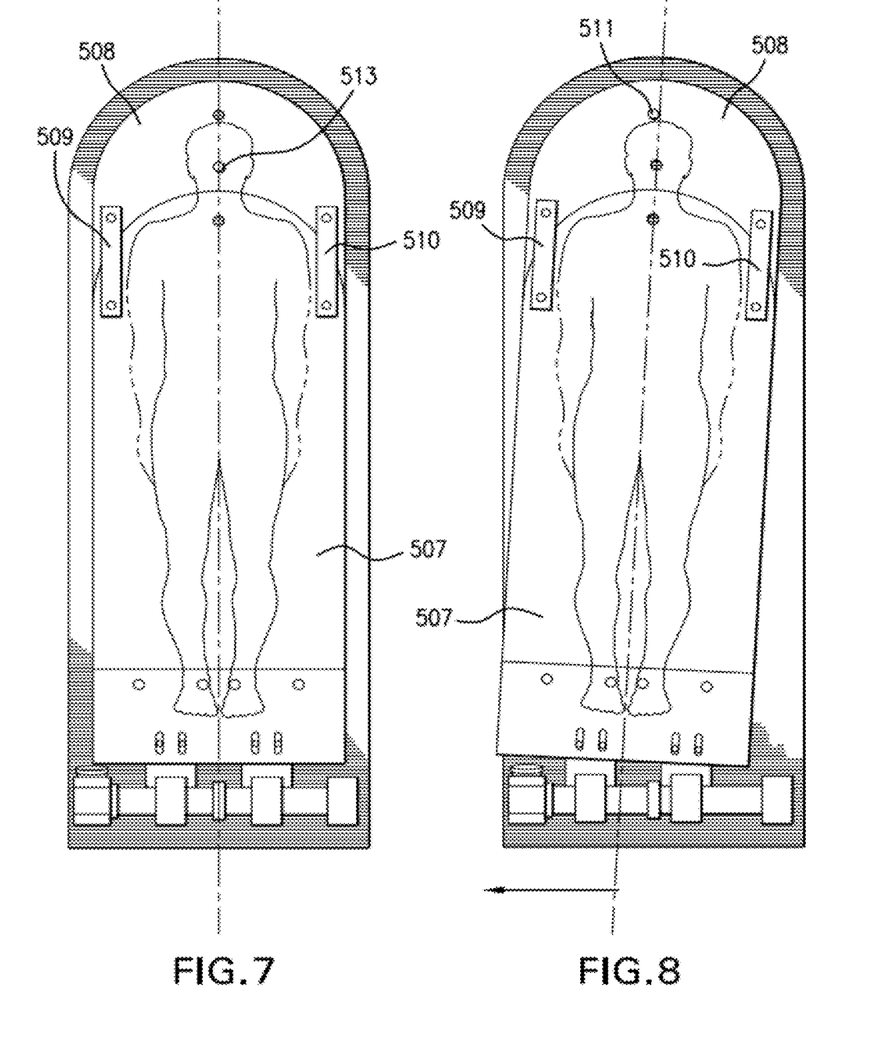
FIGS. 7-9 provide plan views of the embodiment of FIG. 5, showing various configurations of the patient alignment device, according to a first mode of operation.
Figure 9:
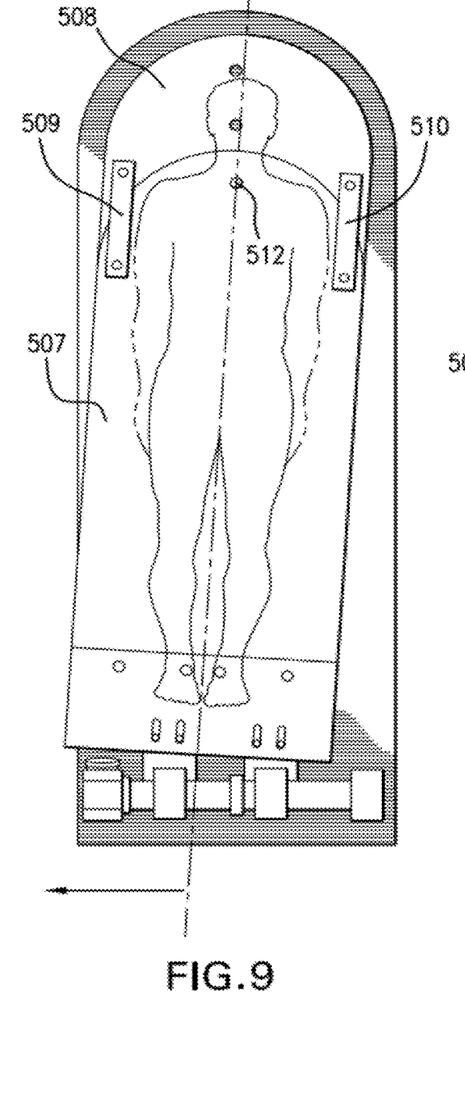

If pin 512 is attached, and the other pins removed, as is shown in FIG. 9, the large board is rotatable around pin 512, and the maximum angle of rotation is relatively large. If pin 511 is attached, and the other pins removed, as is shown in FIG. 8, the large board is rotatable around pin 511, and the maximum angle of rotation is smaller. An intermediate case is shown in FIG. 7, in which pin 513 is attached, and the other pins are removed. In the latter case, the large board rotates around pin 513.

In general, when the maximum angle of rotation is small, and for a given power output available from the motor, the motor is capable of moving a relatively large load. Conversely, when the maximum angle of rotation is large, the motor is only capable of moving a lesser load. In other words, the maximum angle of rotation is inversely related to the weight of the load which can be moved by the motor.

Thus, in general, if the patient is relatively heavy, it is preferable to use the configuration of FIG. 8, in which the large board is rotated around pin 511, the farthest pin from the motor. If the patient is relatively light, it becomes feasible to use the configuration of FIG. 9, in which the large board rotates around pin 512, the closest pin to the motor. The configuration of FIG. 7 comprises an intermediate case.

In the first mode, described above, represented by FIGS. 7-9, the body of the patient is assumed to be straight, but not aligned in the desired direction. Thus, the board segments 507 and 508 are combined to carry and rotate the entire body, and to align the body along the desired axis.

Figure 10:
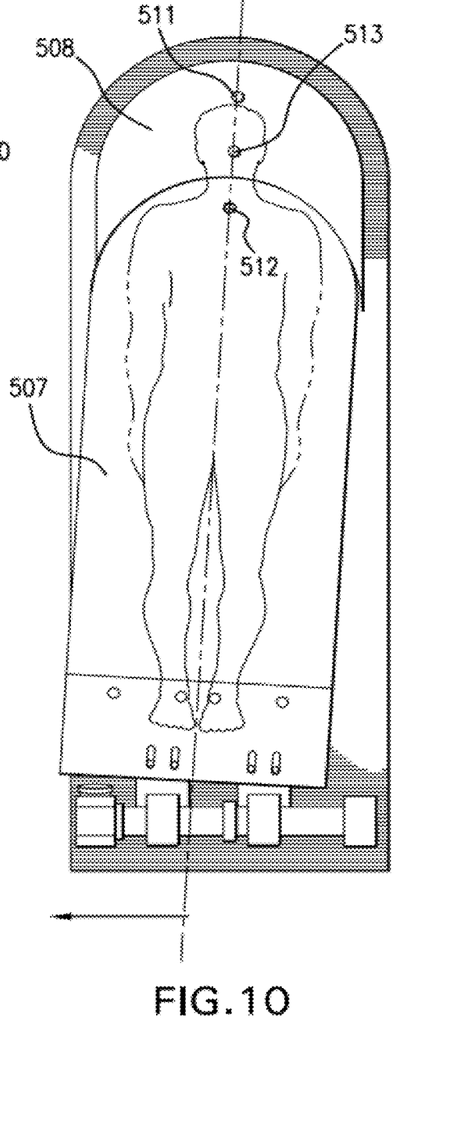
FIG. 10 provides a plan view of the embodiment of FIG. 5, showing a second mode of operation, wherein one segment of a patient support board is allowed to rotate relative to another.

The second mode of operation is illustrated in FIG. 10. In this second mode, the connectors 509 and 510 are removed, and all three pins 511, 512, and 513 are affixed. In this configuration, the first board segment 507 can move independently of second board segment 508, due to the fact that the connectors have been removed. The first board segment rotates around pin 512, while the second board segment remains fixed, due to the engagement of pins 511 and 513 with the table.

This second mode of operation is appropriate for situations in which the body of the patient is curved, and not aligned in the desired direction. Rotation of the first board segment 507 rotates the lower part of the patient's body, while the upper part of the body stays relatively fixed. The flexible spine of the human body allows for a rotation of several degrees to correct the curvature of the body. The first board segment 507 can therefore straighten and align the body of the patient, relative to a desired axis.

Figure 11:
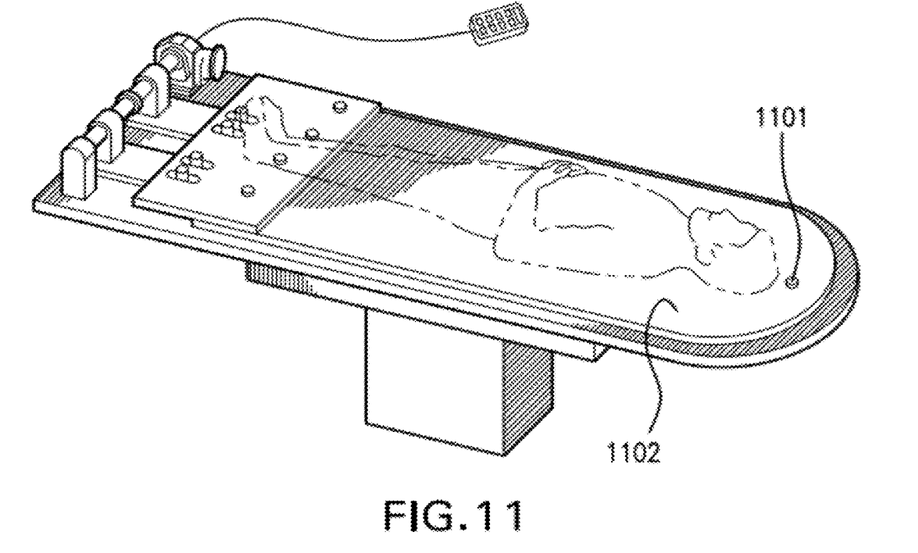
FIG. 11 provides a perspective view of another embodiment of the present invention, in which the table is formed of a single piece.

FIG. 11 provides a perspective view of an alternative to the embodiment of FIG. 5, in which the table is formed of a single piece. In this embodiment, table 1102 rotates about pin 1101, which is positioned at a location near the patient's head. The other components of this embodiment are similar those of the embodiment of FIG. 5, and need not be discussed again here.

The invention has the advantage that it eliminates the need for an operator to make manual adjustments of the position of the body of a patient. By automating such adjustments, the present invention is less physically demanding of the operator, and it provides precision and repeatability that is not achievable by manual adjustments.

During radiation therapy, medical imaging, or many other medical procedures, the operator needs to leave the patient alone in the treatment room to operate the procedure. The device of the present invention allows the operator to re-align the patient remotely, without interrupting the procedure. The invention therefore helps to maintain the consistency and continuity of the medical procedure.

The device of the present invention may be used with existing treatment tables. The invention can be disposed on virtually any hard and flat surface having sufficient area to support the board.

The invention can be modified in various ways, which will be apparent to the reader skilled in the art. The particular means of generating movement of the board or table can be varied. The particular structures used for connecting the motor to the board or table can also be modified.

Another important modification is the location of the pins. For example, in the embodiment of FIG. 2, the pin 204 can be located closer to the middle of the board, instead of at or near one end. Moving the pin towards the middle of the board would enable the angle of rotation to be larger. In the embodiment of FIG. 5, the position of each of the pins could be varied.

The above and other modifications should be understood to be included within the spirit and scope of the following claims.

What is claimed is:

1. A patient alignment device, comprising:
   a) a table,
   b) first and second board segments, the first and second board segments being supported by the table and having generally flat surfaces, the first board segment having a length which is greater than a length of the second board segment, wherein the first and second board segments have mating curved edges such that either of the first and second board segments can rotate while another of said board segments is fixed,
   c) first and second pins, removably inserted in holes formed in the second board segment, and a third pin, removably inserted in a hole formed in the first board segment, wherein all of the pins comprise means for engaging a respective board segment with the table,
   d) a pair of connectors which removably join the first and second board segments, and
   e) a motor, connected to rotate the first board segment,
   wherein the device can be configured in first and second modes,
   wherein a first mode comprises a condition wherein the connectors are affixed to the board segments, and wherein only one of the pins is inserted in one of said holes, and wherein rotation of the first board segment causes the first and second board segments to rotate as one unit, and
   wherein a second mode comprises a condition wherein the connectors are removed from the board segments, and wherein all three of said pins are inserted into their respective holes, and wherein rotation of the first board segment causes the first board segment to rotate while the second board segment is prevented from rotation.

2. The patient alignment device of claim 1, wherein, in said first mode, a choice of which hole in which to engage one of said pins determines a possible angle of rotation of the first and second board segments.

3. The patient alignment device of claim 2, wherein the first pin is positioned farther from the motor than the second pin, and wherein engagement of a selected one of the first pin, the second pin, or the third pin, enables a possible angle of rotation of the first and second board segments which is at a minimum value, an intermediate value, or a maximum value, respectively.

* * * * *